(12) United States Patent
Sanchez et al.

(10) Patent No.: US 11,761,778 B2
(45) Date of Patent: Sep. 19, 2023

(54) SYSTEMS AND METHODS FOR GENERATING CALM OR QUIET ROUTES

(71) Applicant: BlueOwl, LLC, San Francisco, CA (US)

(72) Inventors: Kenneth Jason Sanchez, San Francisco, CA (US); Theobolt N. Leung, San Francisco, CA (US); Patricia Grealish-Rust, Dighton, MA (US)

(73) Assignee: BlueOwl, LLC, San Francisco, CA (US)

( * ) Notice: Subject to any disclaimer, the term of this patent is extended or adjusted under 35 U.S.C. 154(b) by 0 days.

(21) Appl. No.: 18/098,391

(22) Filed: Jan. 18, 2023

(65) Prior Publication Data
US 2023/0204371 A1    Jun. 29, 2023

Related U.S. Application Data

(63) Continuation of application No. 17/749,634, filed on May 20, 2022, now Pat. No. 11,598,642, which is a
(Continued)

(51) Int. Cl.
*G01C 21/36* (2006.01)
*G01C 21/34* (2006.01)
(Continued)

(52) U.S. Cl.
CPC .......... *G01C 21/3484* (2013.01); *A61B 5/024* (2013.01); *A61B 5/18* (2013.01);
(Continued)

(58) Field of Classification Search
CPC ......... A61B 5/024; A61B 5/18; A61B 5/6893; G08G 1/0129; G01C 21/3484; G01C 21/3492; G01C 21/36
See application file for complete search history.

(56) References Cited

U.S. PATENT DOCUMENTS 7,130,743 B2    10/2006    Kudo et al.
8,532,927 B2    9/2013    Joshi et al.
(Continued)

FOREIGN PATENT DOCUMENTS

CN    107133277 A    9/2017

OTHER PUBLICATIONS

Chen et al., "Scenic Planner: Planning scenic travel routes leveraging heterogeneous user-generated digital footprints", Frontiers of Computer Science, 11(1), 2017, pp. 61-74.
(Continued)

*Primary Examiner* — Mathew Franklin Gordon
(74) *Attorney, Agent, or Firm* — Faegre Drinker Biddle & Reath LLP

(57) ABSTRACT

Systems and methods for generating calm or quiet routes are provided. When a user requests navigation directions and indicates a preference for a calm route, a plurality of routes between the origin location and the destination location requested by the user may be identified. Historical sensor data (e.g., including heart rate data, exterior vehicle noise level data, accelerometer data) and traffic data associated with route segments of each of the routes may be analyzed to identify indications of calmness associated with each route segment. Current traffic data associated with the route segments may be analyzed to assign a traffic score representing a level of congestion along the segment and corresponding to a level of insurance risk associated with traversing the segment. Based at least in part upon the indications of calmness and the traffic score associated with each route segment, a route may be selected and presented to the user.

21 Claims, 3 Drawing Sheets

Related U.S. Application Data continuation of application No. 16/795,124, filed on Feb. 19, 2020, now Pat. No. 11,378,410.

(51) Int. Cl.
  *G08G 1/01* (2006.01)
  *A61B 5/00* (2006.01)
  *A61B 5/024* (2006.01)
  *A61B 5/18* (2006.01)

(52) U.S. Cl.
  CPC ........ *A61B 5/6893* (2013.01); *G01C 21/3492* (2013.01); *G01C 21/36* (2013.01); *G08G 1/0129* (2013.01)

(56) References Cited

U.S. PATENT DOCUMENTS

| | | |
|---|---|---|
| 9,074,901 B1 | 7/2015 | Subramanian et al. |
| 9,677,886 B2 | 6/2017 | Didjusto et al. |
| 9,709,413 B2 | 7/2017 | Caceres et al. |
| 2003/0009281 A1 | 1/2003 | Whitham |
| 2018/0281858 A1 | 10/2018 | Griffith |
| 2021/0123749 A1 | 4/2021 | Kreig et al. |

OTHER PUBLICATIONS

Zheng et al., "GPS View: A scenic driving route planner. ACM Transactions on Multimedia Computing, Communications and Applications", 9(1), Feb. 2013, pp. 3:1-3:18.

SYSTEMS AND METHODS FOR GENERATING CALM OR QUIET ROUTES

This application is a continuation of U.S. patent application Ser. No. 17/749,634, filed May 20, 2022, which is a continuation of U.S. patent application Ser. No. 16/795,124, filed Feb. 19, 2020, the entire disclosures of which are incorporated by reference herein for all purposes.

FIELD OF THE DISCLOSURE

The present disclosure generally relates to vehicle safety and, more particularly, to systems and methods for generating calm or quiet routes.

BACKGROUND

The background description provided herein is for the purpose of generally presenting the context of the disclosure. Work of the presently named inventors, to the extent it is described in the background section, as well as aspects of the description that may not otherwise qualify as prior art at the time of filing, are neither expressly nor impliedly admitted as prior art against the present disclosure.

While current navigation applications may generate vehicle routes that provide the fastest or shortest drive between an origin location and a destination location, current navigation applications typically do not account for driver stress level when generating a route. However, certain vehicle routes may be particularly stressful for some drivers. For example, certain routes, such as, e.g., loud routes, congested routes, routes with large numbers of lanes, routes including uneven terrain, etc., may be stressful for certain drivers. However, as a driver's stress level rises, he or she may be more likely to get into a vehicle accident.

SUMMARY

In one aspect, a computer-implemented method of generating a calm route is provided. The method comprises: receiving, by one or more processors, a user request for navigation directions from an origin location to a destination location, wherein the user request includes an indication of a user preference for a calm route; identifying, by one or more processors, based at least in part upon map data, a plurality of routes between the origin location and the destination location; analyzing, by one or more processors, historical sensor data associated with route segments of each of the plurality of routes between the origin location and the destination location to identify indications of calmness associated with each route segment, wherein the historical sensor data is received from at least a heart rate sensor, a microphone fixed to a vehicle and configured to receive noise data from an exterior of the vehicle, an accelerometer, and an external traffic database; wherein the historical sensor data associated with each route segment includes: 1) heart rate data associated with operators of vehicles captured while driving the route segment, 2) noise data received from exteriors of vehicles traveling along the route segment, 3) accelerometer data indicative of hard breaking and acceleration events captured along the route segment, and 4) historical traffic data along the route segment; assigning, by one or more processors, a score to current traffic data associated with the route segments of each of the plurality of routes between the origin location and the destination location to represent a level of congestion along the segment, where the score corresponds to a level of insurance risk associated with traversing the segment; selecting, by one or more processors, one of the plurality of routes between the origin location and the destination location based at least in part upon the indications of calmness associated with the route segments of the route and the score assigned to the current traffic data; and presenting, by one or more processors, the selected route from the origin location to the destination location to a user.

In another aspect, a computer system for generating a calm route, comprising: one or more processors; and a non-transitory program memory communicatively coupled to the one or more processors and storing executable instructions. The executable instructions, when executed by the one or more processors, cause the computer system to: receive a user request for navigation directions from an origin location to a destination location, wherein the user request includes an indication of a user preference for a calm route; identify, based at least in part upon map data, a plurality of routes between the origin location and the destination location; analyze historical sensor data associated with route segments of each of the plurality of routes between the origin location and the destination location to identify indications of calmness associated with each route segment, wherein the historical sensor data is received from at least a heart rate sensor, a microphone fixed to a vehicle and configured to receive noise data from an exterior of the vehicle, an accelerometer, and an external traffic database; wherein the historical sensor data associated with each route segment includes: 1) heart rate data associated with operators of vehicles captured while driving the route segment, 2) noise data received from exteriors of vehicles traveling along the route segment, 3) accelerometer data indicative of hard breaking and acceleration events captured along the route segment, and 4) historical traffic data along the route segment; assign a score to current traffic data associated with the route segments of each of the plurality of routes between the origin location and the destination location to represent a level of congestion along the segment, where the score corresponds to a level of insurance risk associated with traversing the segment; select one of the plurality of routes between the origin location and the destination location based at least in part upon the indications of calmness associated with the route segments of the route and the score assigned to the current traffic data; and present the selected route from the origin location to the destination location to a user.

In still another aspect, a tangible, non-transitory computer-readable medium for generating a calm route is provided. The tangible, non-transitory computer-readable medium stores executable instructions that, when executed by at least one processor of a computer system, cause the processor to: receive a user request for navigation directions from an origin location to a destination location, wherein the user request includes an indication of a user preference for a calm route; identify, based at least in part upon map data, a plurality of routes between the origin location and the destination location; analyze historical sensor data associated with route segments of each of the plurality of routes between the origin location and the destination location to identify indications of calmness associated with each route segment, wherein the historical sensor data is received from at least a heart rate sensor, a microphone fixed to a vehicle and configured to receive noise data from an exterior of the vehicle, an accelerometer, and an external traffic database; wherein the historical sensor data associated with each route segment includes: 1) heart rate data associated with operators of vehicles captured while driving the route segment, 2)

noise data received from exteriors of vehicles traveling along the route segment, 3) accelerometer data indicative of hard breaking and acceleration events captured along the route segment, and 4) historical traffic data along the route segment; assign a score to current traffic data associated with the route segments of each of the plurality of routes between the origin location and the destination location to represent a level of congestion along the segment, where the score corresponds to a level of insurance risk associated with traversing the segment; select one of the plurality of routes between the origin location and the destination location based at least in part upon the indications of calmness associated with the route segments of the route and the score assigned to the current traffic data; and present the selected route from the origin location to the destination location to a user.

Depending upon the embodiment, one or more benefits may be achieved. These benefits and various additional objects, features and advantages of the present disclosure can be fully appreciated with reference to the detailed description and accompanying drawings that follow.

BRIEF DESCRIPTION OF THE DRAWINGS

The figures described below depict various aspects of the systems and methods disclosed herein. Advantages will become more apparent to those skilled in the art from the following description of the embodiments which have been shown and described by way of illustration. As will be realized, the present embodiments may be capable of other and different embodiments, and their details are capable of modification in various respects. Accordingly, the drawings and description are to be regarded as illustrative in nature and not as restrictive.

DETAILED DESCRIPTION

As discussed above, while current navigation applications may generate vehicle routes that provide the fastest or shortest drive between an origin location and a destination location, current navigation applications typically do not account for driver stress level when generating a route. However, certain vehicle routes may be particularly stressful for some drivers. For example, certain routes, such as, e.g., loud routes, congested routes, routes with large numbers of lanes, routes including uneven terrain, etc., may be stressful for certain drivers. However, as a driver's stress level rises, he or she may be more likely to get into a vehicle accident.

The present application provides systems and methods for generating calm or quiet routes. When a driver indicates that he or she wishes to take a calm or quiet route from an origin location to a destination location, a mobile device application may generate a calm or quiet route by analyzing sensor data associated with historical routes or route segments driven by a particular driver or by a driver population to determine and/or predict which routes or route segments will be associated with calm drivers and/or quiet routes. For example, softer or less frequent braking, fewer accelerations, more consistent velocity, less speeding, and less honking may be associated with calmer driving. Moreover, sensor data indicative of quiet vehicle interior or surroundings, or indicative of nature sounds (e.g., birds, ocean waves, crickets) may be associated with calmer driving. Additionally, a lower driver heart rate (e.g., as determined by a wearable fitness tracker) may be associated with calmer driving. Furthermore, routes with fewer lanes and/or less congestion or less construction may be associated with calmer driving. Advantageously, the systems and methods provided by the present application provide calmer or quieter routes for drivers, which may reduce stress levels for drivers and decrease the risk of vehicle accidents.

Figure 1:
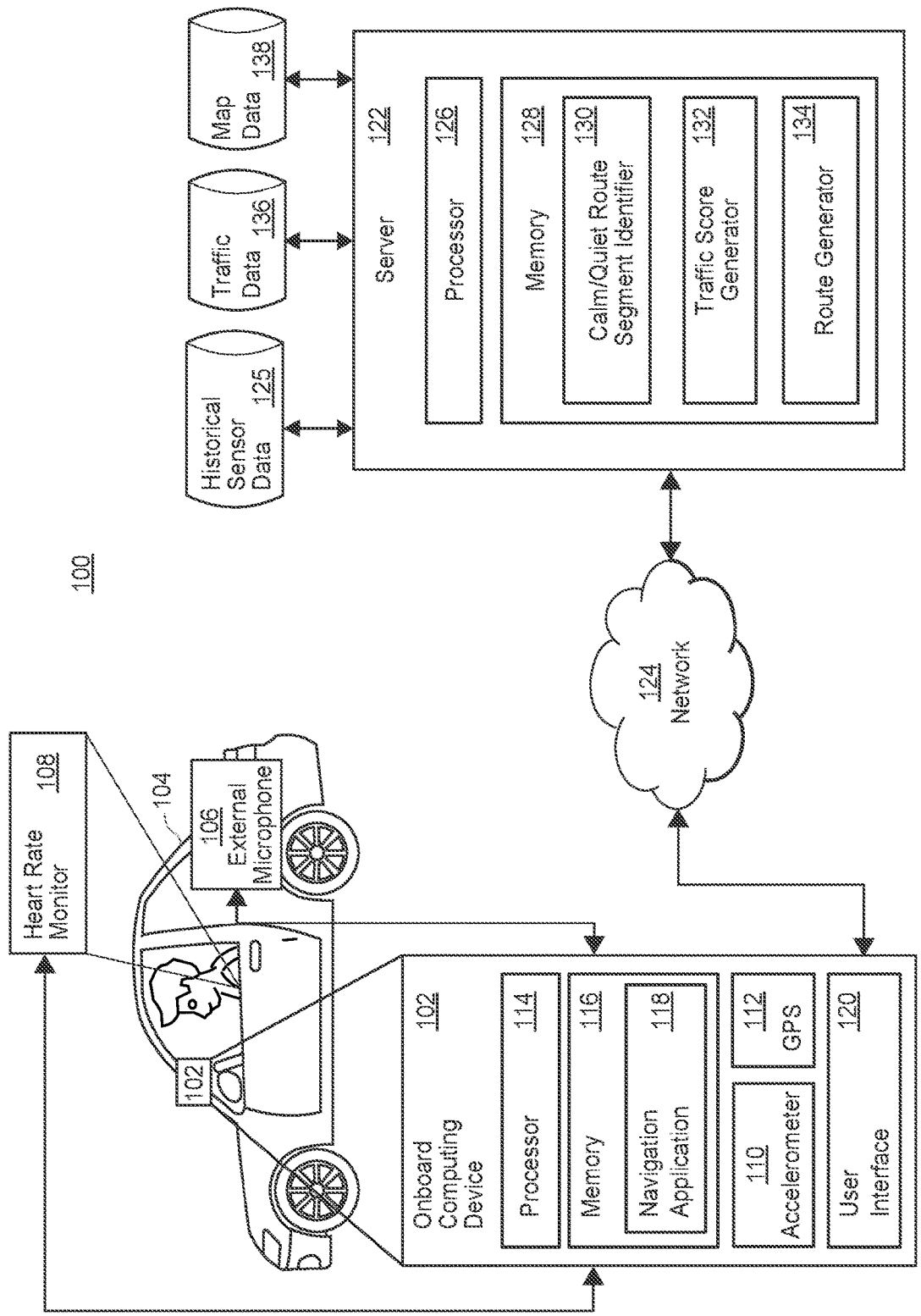
FIG. 1 illustrates a block diagram of an exemplary system for generating calm or quiet routes, in accordance with some embodiments.

FIG. 1 illustrates a block diagram of an exemplary system 100 for generating calm or quiet routes, in accordance with some embodiments. The high-level architecture illustrated in FIG. 1 may include both hardware and software applications, as well as various data communications channels for communicating data between the various hardware and software components, as is described below. The system 100 may include one or more onboard computing devices 102, which may each be positioned within or otherwise associated with a respective vehicle 104 (which may be, e.g., a car, a truck, a boat, a motorcycle, a motorized scooter, or any other vehicle). For instance, an onboard computing device 102 may be built into the vehicle 104, or may be a mobile device (such as, e.g., a smart phone, a smart watch, a GPS system, etc.) associated with a driver or operator of the vehicle 104.

Each onboard computing device 102 may communicate with various sensors to receive sensor data captured as the respective vehicles 104 travel along various routes. This sensor data may include sensor data captured by onboard sensors associated with the vehicle, such as a microphone 106 configured to capture noise data from an exterior of the vehicle 104. Additionally, the onboard computing devices 102 may communicate with sensor devices associated with a driver or operator of the vehicle 104, such as, e.g., a heart rate monitor 108 (e.g., a dedicated heart rate monitor worn by the driver or operator, or a smart watch or wearable fitness tracker worn by the driver or operator) configured to capture heart rate data associated with the driver or operator of the vehicle 104. Furthermore, the onboard computing devices 102 may include motion sensors 110 such as accelerometers or gyroscopes configure to capture instances of acceleration and/or instances of hard braking, and/or location sensors 112 such as global positioning sensors configured to capture location data, or may communicate with external accelerometers and/or location sensors positioned within the vehicle 104.

Furthermore, each onboard computing device 102 may include one or more processors 114, such as one or more microprocessors, controllers, and/or any other suitable type of processors, and a memory 116 (e.g., volatile memory, non-volatile memory) accessible by the respective one or more processors 114, (e.g., via a memory controller). The one or more processors 114 may interact with the memory 116 to obtain, for example, computer-readable instructions stored in the memory 116. In particular, the computer-readable instructions stored on the memory 116 may include instructions for executing a navigation application 118 configured to generate and display navigation directions for a calm route for a user of the onboard computing device 102. Moreover, the computer-readable instructions stored on the memory 116 may include instructions for carrying out one or more of the steps of the method 300 described in greater detail below with respect to FIG. 3.

Furthermore, each onboard computing device 102 may include a user interface 120, which may be configured to receive input from users (e.g., requests for navigation directions, indications of preferences for calm or quiet routes, etc.) and/or to display information to users (e.g., navigation directions generated by the navigation application 118).

Each onboard computing device 102 may be configured to communicate with a server 122, e.g., via a network 124. For instance, each onboard computing device 102 may communicate data captured by sensors such as the microphone 106, the heart rate monitor 108, the motion sensor 110, the location sensor 112, etc., to the server 122. In some examples, the server 122 may be configured to store the sensor data from each of the onboard computing devices 102 associated with various respective vehicles 104 in a historical sensor database 125. Furthermore, each onboard computing device 102 may communicate user input received via the user interface 120, such as requests for navigation directions, indications of preferences for calm or quiet routes, etc., to the server 122.

The server 122 may include one or more processors 126, such as one or more microprocessors, controllers, and/or any other suitable type of processors, and a memory 128 (e.g., volatile memory, non-volatile memory) accessible by the respective one or more processors 126, (e.g., via a memory controller). The one or more processors 126 may interact with the memory 128 to obtain, for example, computer-readable instructions stored in the memory 128. In particular, the computer-readable instructions stored on the memory 126 may include instructions for executing various applications, such as, e.g., a calm/quiet route segment identifier 130, a traffic score generator 132, and a route generator 134. As the processors 126 execute the applications, the server 122 may access various databases, which may be internal or external, such as the historical sensor database 125 configured to store historical sensor data captured by the onboard computing devices 102 (and/or from other sources), a traffic database 136 storing historical and/or current traffic data associated with various routes and/or route segments, a map database 138 storing map data indicating various routes and/or route segments as well as locations associated with various addresses, weather databases (not shown), etc.

The calm/quiet route segment identifier 130 may be configured to analyze various route segments in order to identify indications of calmness associated with each route segment. In particular, the calm/quiet route segment identifier 130 may analyze historical sensor data from the historical sensor data database 125 in order to identify indications of calmness associated with each route segment. For example, the calm/quiet route segment identifier 130 may correlate historical location data captured at each vehicle at various times with historical noise data, heart rate data, and acceleration and/or gyroscope data captured at the same times to determine locations associated with each noise data point, each heart rate data point, and each acceleration and/or gyroscope data point. In particular, the calm/quiet route segment identifier 130 may determine which locations correspond to sensor data associated with calm driving. For example, the calm/quiet route segment identifier 130 may identify locations in which the historical noise data indicates average exterior volumes below a certain threshold value, and/or locations in which the historical noise data indicates audible exterior noises associated with natural environments, indicating that route segments including those locations generally include fewer human-generated noises, such as vehicle honking, yelling, construction noises, etc., and are consequently more calm. As another example, the calm/quiet route segment identifier 130 may identify locations in which the historical heart rate data indicates an average operator heart rate below a predetermined heart rate threshold, indicating that drivers driving route segments including those locations are typically calm. Furthermore, as still another example, the calm/quiet route segment identifier 130 may identify locations in which the historical accelerometer and/or gyroscope data indicates an average number of hard breaking and/or acceleration events that is below a certain threshold value, indicating that route segments including these locations typically include fewer stops, and accordingly may be associated with more calm driving.

In some examples, the calm/quiet route segment identifier 130 may analyze historical traffic data (e.g., from the traffic database 136) in order to identify indications of calmness associated with each route segment. For instance, historical traffic data indicating a historical level of congestion below a certain threshold value may be associated with more calm driving. For instance, a historical low number of vehicles on a particular route segment and/or a historically low ratio of vehicles per mile, e.g., below a certain threshold value, may indicate that the route segment has historically been a calm route segment.

In particular, the calm/quiet route segment identifier 130 may calculate a score associated with the route segment (e.g., a "calmness score"), e.g., based at least in part upon a number of indications of calmness and/or quietness associated with each route segment and/or a degree of calmness and/or quietness associated with each route segment. For instance, the calmness score may be calculated as a percentage out of 100, as a number on a scale of 1-10, as a numerical "grade" (e.g., A, B, C, etc.), etc. Moreover, in some examples, the indications of calmness and/or quietness associated with each route segment may include a time associated with each indication. For instance, a route may be very calm at particular times of day but not as calm at other times of day.

The traffic score generator 132 may be configured to analyze current traffic data (e.g., from the traffic database 136) associated with various route segments in order to calculate a traffic score representing a level of congestion along each route segment. In particular, the traffic score may correspond to a level of insurance risk associated with traversing the segment. For instance, a higher score may indicate a greater degree of congestion (e.g., a larger number of vehicles currently traversing the route segment, a higher ratio of vehicles per mile, etc.), and may accordingly be associated with a higher level of insurance risk (e.g., a greater likelihood of a vehicle accident). As discussed above with respect to the calmness score, the congestion score may be calculated as a percentage out of 100, as a number on a scale of 1-10, as a numerical "grade" (e.g., A, B, C, etc.), etc.

The route generator 134 may generate routes based at least in part upon user requests for navigation directions received by the server 122 from onboard computing devices 102. A particular user request for navigation directions may include an indication of an origin location and a destination location, as well as an indication of whether a user has indicated a preference for a calm route. The route generator 134 may identify a plurality of routes between the origin location and the destination location using map data from the map database 138. If there is no indication that a user has indicated a preference for a calm route, the route generator 134 may select a route based at least in part upon factors such as which route is associated with the shortest driving distance, which route is associated with the shortest driving time, etc. If there is an indication that the user has indicated a preference for a calm route, the route generator 134 may select a route based at least in part upon the indications of calmness (or "calmness score") and the traffic score associated with the route segments of each of the identified plurality of routes. For example, if there is an indication that the user has indicated a preference for a calm route, the route generator 134 may select a route whose route segments have a higher calmness score and a lower traffic rather than a route associated with the shortest driving distance or the shortest driving time. The route generator 134 may communicate an indication of the selected route to an onboard computing device 102 associated with the user who made the request for navigation directions, and the navigation application 118 of the onboard computing device 102 may cause the route to be displayed via the user interface 120 of the onboard computing device 102.

Moreover, the computer-readable instructions stored on the memory 128 may include instructions for carrying out any of the steps of the method 300 described in greater detail below with respect to FIG. 3. Furthermore, in some examples, steps described above as being performed by the processor 126 of the server 122 may be performed by the processor 114 of the onboard computing device 102, or vice versa.

Figure 2A:
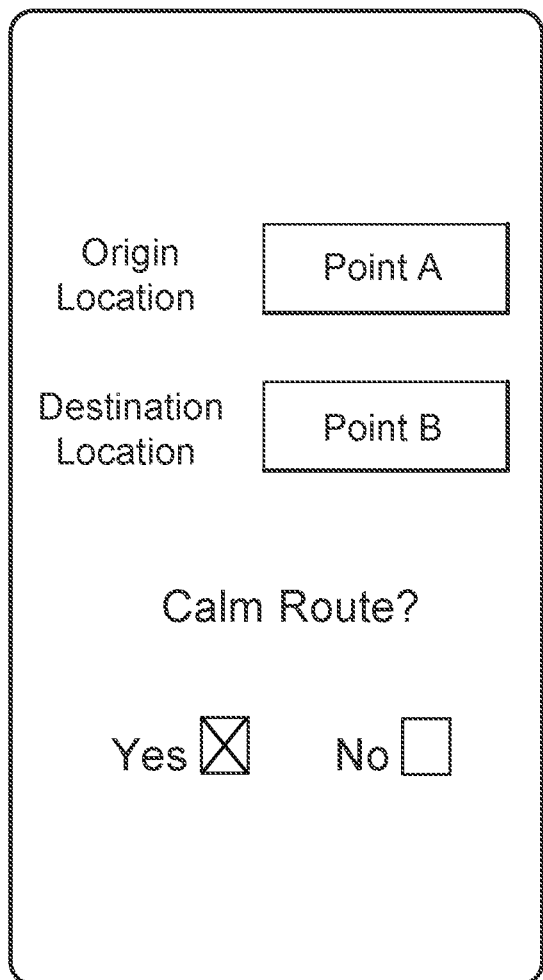
FIG. 2A illustrates an exemplary user interface display, in accordance with some embodiments.
Figure 2B:
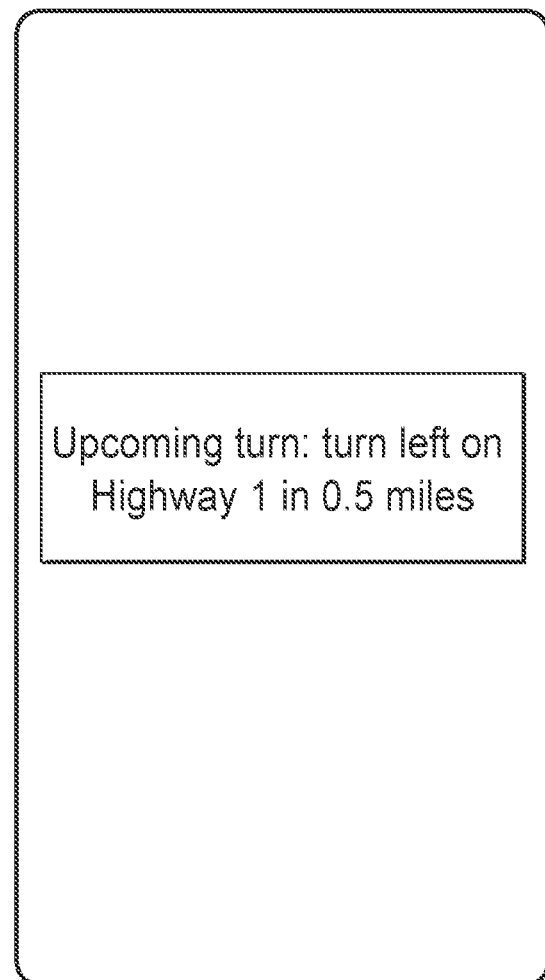
FIG. 2B illustrates an exemplary user interface display, in accordance with some embodiments.

FIG. 2A and FIG. 2B illustrate exemplary user interface displays, in accordance with some embodiments. For instance, as shown in FIG. 2A, a user may provide input related to a request for navigation directions via a user interface (e.g., user interface 120 as shown in FIG. 1), including an indication of an origin location, a destination location, and an indication of whether or not the user has a preference for a calm route. As shown in FIG. 2B, the user interface display may show notifications indicating upcoming maneuvers (e.g., "turn left on Highway 1 in 0.5 miles") of a selected route. In other examples (not shown), the user interface display may include a graphic display of the route and associated maneuvers.

Figure 3:
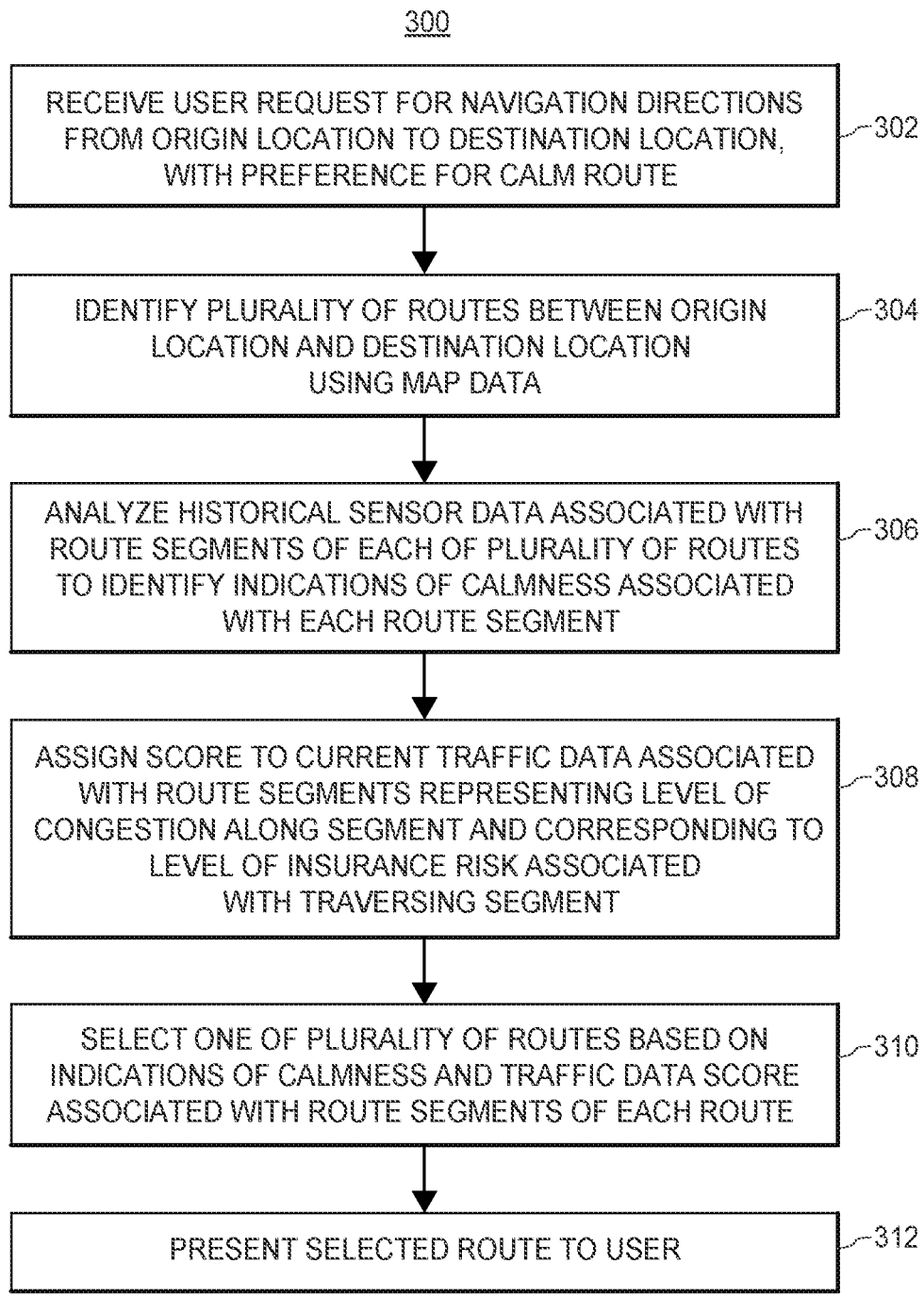
FIG. 3 illustrates a flow diagram of an exemplary method for generating calm or quiet routes, in accordance with some embodiments.

Referring now to FIG. 3, a flow diagram of an exemplary method 300 for generating calm or quiet routes is illustrated, in accordance with some embodiments. One or more steps of the method 300 may be implemented as a set of instructions stored on a computer-readable memory and executable on one or more processors.

The method 300 may begin when a user request for navigation directions from an origin location to a destination location is received (block 302). In particular, a user request may include an indication of a user preference for a calm route. For example, a user may indicate his or her preference for a calm or quiet route using via a user interface of a mobile computing device. In some examples, the user may indicate his or her preference for a calm or quiet route when requesting the navigation directions, while in other examples, the user may indicate a general preference for calm or quiet routes for all requests for navigation directions. For instance, some users may only prefer calmer or quieter routes when they are not rushed, while other users may prefer calmer or quieter routes generally, i.e., during all or most trips.

In some examples, the indication of the user request for the calm route may be determined based at least in part upon current heart rate data associated with the user. For example, current heart rate data associated with a user may be obtained, e.g., from a smart watch, wearable fitness tracker, etc. A higher user heart rate may be an indication of stress in the user, and may indicate that the user might prefer a calm or quiet route. Accordingly, a calm or quiet route may be selected for a user having a high current heart rate (e.g., a heart rate above a certain threshold heart rate), or a prompt may be provided to the user, including an option for a user to select a calm or quiet route.

A plurality of routes between the origin location and the destination location may be identified (block 304) based at least in part upon map data. Each route may include one or more maneuvers (e.g., turns, stops, etc.) as well as a number of route segments, i.e., portions of the route between each maneuver. For example, a first route between an origin ("Point A") and a destination ("Point B") may be to turn left from Point A onto Highway 1, drive for 2 miles, turn right on Road 2, drive for 1 mile, and then turn left on Street 3 and drive for 0.5 miles to reach Point B. The 2 miles on Highway 1, the 1 mile on Road 2, and the 0.5 miles on Street 3 may each be route segments of the first route. A second route between Point A and Point B may be to drive straight on Parkway 4 for 1 mile, then turn left on Street 3 and drive for 2.5 miles to reach point B. The 1 mile on Parkway 4, and the 2.5 miles on Street 3 may each be route segments of the second route.

Historical sensor data associated with route segments of each of the plurality of routes between the origin location and the destination location may be analyzed (block 306) to identify indications of calmness (and/or quietness) associated with each route segment. The historical sensor data may include historical data received from sensors including, e.g., a heart rate sensor, a microphone fixed to a vehicle and configured to receive noise data from an exterior of the vehicle, an accelerometer, an external traffic database, etc. For example, the historical sensor data associated with each route segment may include heart rate data associated with operators of vehicles captured while driving the route segment, noise data received from exteriors of vehicles traveling along the route segment, accelerometer data indicative of hard breaking and acceleration events captured along the route segment, historical traffic data along the route segment, etc. The historical sensor data may include historical sensor data associated with the user from historical instances in which the user drove along the route segments, or historical sensor data associated with other users from historical instances in which the other users traveled along each route segment.

In some examples, a number of indications of calmness and/or quietness associated with each route segment and/or a degree of calmness and/or quietness associated with each route segment may be used to calculate a score associated with the route segment (e.g., a "calmness score"). For instance, the calmness score may be calculated as a percentage out of 100, as a number on a scale of 1-10, as a numerical "grade" (e.g., A, B, C, etc.), etc. Moreover, in some examples, the indications of calmness and/or quietness associated with each route segment may include a time associated with each indication. For instance, a route may be very calm at particular times of day but not as calm at other times of day.

For example, identifying one or more indications of calmness associated with each route segment using the historical sensor data may include identifying one or more instances in which the microphone receives noise data below a predetermined volume threshold and/or noise data indicative of sounds associated with natural environments. That is, historical noise data indicative of sounds below a predetermined volume threshold captured by microphones associated with vehicles traveling along a route segment may indicate that the route segment has historically been a calm route segment, which may factor into a calmness score for the route segment. Moreover, historical noise data indicative of sounds associated with natural environments (e.g., waves, birds, crickets, leaves moving in the wind, etc.) captured by microphones associated with vehicles traveling along a route segment may also indicate that the route segment has historically been a calm route segment, which may factor into a calmness score for the route segment. In contrast, noise data indicative of loud sounds and/or noise data indicating a lack of sounds associated with natural environments captured as a vehicle travels along a route segment may indicate that the route segment is less calm or less quiet.

Moreover, identifying one or more indications of calmness associated with each route segment using the historical sensor data may include identifying one or more instances in which the historical heart rate data indicates an average operator heart rate below a predetermined heart rate threshold captured as the vehicle travels along the route segment. That is, generally speaking, calm drivers will have lower heart rates while drivers experiencing stress will have higher heart rates. Accordingly, in some examples, an average historical heart rate below a predetermined heart rate threshold for drivers traveling a particular route segment may indicate that the route segment has historically been a calm route segment, which may factor into a calmness score for the route segment.

As another example, identifying one or more indications of calmness associated with each route segment using the historical sensor data may include identifying one or more instances in which the accelerometer data indicates a number of hard breaking and/or acceleration events that is below a certain threshold value. That is, drivers may be less calm when they need to brake and accelerate frequently, but may be calmer when they can drive steadily with fewer braking and/or acceleration events. Accordingly, in some examples, a number of historical hard braking and/or acceleration events associated with a route segment below a certain threshold value may indicate that the route segment has historically been a calm route segment, which may factor into a calmness score for the route segment.

Additionally, as another example, identifying one or more indications of calmness associated with each route segment using the historical sensor data may include identifying one or more instances in which the historical traffic data indicates a level of congestion below a certain threshold value. For instance, a historical low number of vehicles on a particular route segment and/or a historically low ratio of vehicles per mile, e.g., below a certain threshold value, may indicate that the route segment has historically been a calm route segment, which may factor into a calmness score for the route segment.

Furthermore, in some examples, additional or alternative historical and current sensor data (and/or historical and current data from external databases) associated with each of the route segments may be used to identify indications of calmness associated with the route segments. For example, other historical data may be correlated with the historical heart rate data, historical noise data, historical accelerometer data and/or historical traffic data associated with the route segment in order to identify other sensor data indicative of calmness. For instance, machine learning techniques may be used to identify other sensor data indicative of calmness, in some case specifically for a particular user. As one example, certain historical weather data for locations associated with route segments may be associated with increased heart rate for certain users, or may cause increased hard braking events for a particular user. Accordingly, for that particular user, a reduced indication of calmness or a reduced calmness score may be assigned to a route segment associated with certain current weather data.

A score may be assigned (block 308) to current traffic data associated with the route segments of each of the plurality of routes between the origin location and the destination location to represent a level of congestion along the segment. In particular, the score may correspond to a level of insurance risk associated with traversing the segment. For instance, a higher score may indicate a greater degree of congestion (e.g., a larger number of vehicles currently traversing the route segment, a higher ratio of vehicles per mile, etc.), and may accordingly be associated with a higher level of insurance risk (e.g., a greater likelihood of a vehicle accident).

One of the plurality of routes between the origin location and the destination location may be selected (block 310) based at least in part upon the indications of calmness associated with the route segments of the route (and/or a calmness score associated with each of the route segments) and the congestion score assigned to the current traffic data. For instance, a route comprising route segments having higher calmness scores and lower traffic scores may be selected instead of a route comprising route segments having lower calmness scores and/or higher traffic scores. In some examples, the calmness score and the traffic score for each route segment may be combined into a combined route segment score, and the route comprising route segments having the best combined route segment score maybe selected. In some examples, selecting the route may further include determining a time of day at which the user is planning to drive the route and/or an expected time of day at which the user would travel each route segment of the route (e.g., in order to factor the fact that certain route segments may be calmer at certain times of day into the selection of the route).

The selected route from the origin location to the destination location may be presented (block 312) to the user, e.g., via a user interface. For example, the route may be provided as a map, as a list of maneuvers, etc.

With the foregoing, an insurance customer may opt-in to a rewards, insurance discount, or other type of program. After the insurance customer provides their affirmative consent, an insurance provider remote server may collect data from the customer's mobile device, smart home controller, or other smart devices—such as with the customer's permission or affirmative consent. The data collected may be related to insured assets before (and/or after) an insurance-related event, including those events discussed elsewhere herein. In return, risk averse insureds may receive discounts or insurance cost savings related to home, renters, personal articles, auto, and other types of insurance from the insurance provider.

In one aspect, data, including the types of data discussed elsewhere herein, may be collected or received by an insurance provider remote server, such as via direct or indirect wireless communication or data transmission from a smart home controller, mobile device, or other customer computing device, after a customer affirmatively consents or otherwise opts-in to an insurance discount, reward, or other program. The insurance provider may then analyze the data received with the customer's permission to provide benefits to the customer. As a result, risk averse customers may receive insurance discounts or other insurance cost savings based at least in part upon data that reflects low risk behavior and/or technology that mitigates or prevents risk to (i) insured assets, such as homes, personal belongings, or vehicles, and/or (ii) home or apartment occupants.

Although the foregoing text sets forth a detailed description of numerous different embodiments, it should be understood that the legal scope of the disclosed may be defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a non-transitory, machine-readable medium) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that may be permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that may be temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules may provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connect the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it may be communicatively coupled. A further hardware module may then, at a later time, access the memory device to retrieve and process the stored output. Hardware modules may also initiate communications with input or output devices, and may operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but deployed across a number of machines. In some example embodiments, the processor or processors may be located in a single location (e.g., within an office environment, or as a server farm), while in other embodiments the processors may be distributed across a number of locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, non-volatile memory, or a combination thereof), registers, or other machine components that receive, store, transmit, or display information.

As used herein any reference to "one embodiment" or "an embodiment" means that a particular element, feature, structure, or characteristic described in connection with the embodiment may be included in at least one embodiment. The appearances of the phrase "in one embodiment" in various places in the specification are not necessarily all referring to the same embodiment.

As used herein, the terms "comprises," "comprising," "may include," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also may include the plural unless it is obvious that it is meant otherwise.

This detailed description is to be construed as examples and does not describe every possible embodiment, as describing every possible embodiment would be impractical, if not impossible. One could implement numerous alternate embodiments, using either current technology or technology developed after the filing date of this application.

Although specific embodiments of the present disclosure have been described, it will be understood by those of skill in the art that there are other embodiments that are equivalent to the described embodiments. Accordingly, it is to be understood that the present disclosure is not to be limited by the specific illustrated embodiments.

What is claimed is:

1. A computer-implemented method of generating a route, the method comprising:
    receiving, by one or more processors, a navigation request from an origin location to a destination location, wherein the navigation request includes an indication of a user preference of a user for a calm route;
    identifying, by the one or more processors, based at least in part upon map data, a plurality of routes between the origin location and the destination location;
    receiving sensor data associated with one or more route segments of each route of the plurality of routes between the origin location and the destination location;
    identifying, by the one or more processors, one or more indications of calmness associated with each route segment of the one or more route segments by analyzing the sensor data;
    determining a calmness score associated with each route segment of the one or more route segments based upon the one or more identified indications of calmness associated with each route segment of the one or more route segments; and
    selecting, by the one or more processors, one route of the plurality of routes between the origin location and the destination location based at least in part upon the calmness score associated with each route segment of the one or more route segments.

2. The method of claim 1, wherein the calmness score is determined based at least in part upon a number of the one or more indications of calmness and a degree of calmness associated with each route segment of the one or more route segments.

3. The method of claim 1, wherein the sensor data includes historical sensor data.

4. The method of claim 1, wherein the sensor data includes current traffic data.

5. The method of claim 4, wherein the sensor data was collected by one or more sensors, wherein the sensor data includes at least one selected from a group consisting of: 1) heart rate data associated with operators of vehicles captured while driving a route segment, 2) noise data received from exteriors of vehicles traveling along a route segment, 3) accelerometer data indicative of hard braking and acceleration events captured along a route segment, and 4) traffic data along a route segment.

6. The method of claim 5, wherein the identifying one or more indications of calmness includes identifying one or more instances in which the noise data is below a predetermined volume threshold.

7. The method of claim 4, further comprising:
    assigning, by the one or more processors, a traffic score to the current traffic data associated with each route segment the one or more route segments of each route of the plurality of routes between the origin location and the destination location to represent a level of congestion along the one or more segments;
    wherein the identifying one or more indications of calmness comprises identifying the one or more indications of calmness associated with each route segment of the one or more route segments based at least in part on the traffic score associated with each route segment of the one or more route segments.

8. A computer system for generating a route, the system comprising:
    one or more memories storing instructions; and
    one or more processors configured to execute the instructions and configured to:
        receive a navigation request from an origin location to a destination location, wherein the navigation request includes an indication of a user preference of a user for a calm route;
        identify, based at least in part upon map data, a plurality of routes between the origin location and the destination location;
        receive sensor data associated with one or more route segments of each route of the plurality of routes between the origin location and the destination location;
        identify one or more indications of calmness associated with each route segment of the one or more route segments by analyzing the sensor data;
        determine a calmness score associated with each route segment of the one or more route segments based upon the one or more identified indications of calmness associated with each route segment of the one or more route segments; and
        select one route of the plurality of routes between the origin location and the destination location based at least in part upon the calmness score associated with each route segment of the one or more route segments.

9. The computer system of claim 8, wherein the calmness score is determined based at least in part upon a number of the one or more indications of calmness and a degree of calmness associated with each route segment of the one or more route segments.

10. The computer system of claim 8, wherein the sensor data includes historical sensor data.

11. The computer system of claim 8, wherein the sensor data includes current traffic data.

12. The computer system of claim 11, wherein the sensor data was collected by one or more sensors, wherein the sensor data includes at least one selected from a group consisting of: 1) heart rate data associated with operators of vehicles captured while driving a route segment, 2) noise data received from exteriors of vehicles traveling along a route segment, 3) accelerometer data indicative of hard braking and acceleration events captured along a route segment, and 4) traffic data along a route segment.

13. The computer system of claim 12, wherein to identify one or more indications of calmness, the one or more processors are configured to identify one or more instances in which the noise data is below a predetermined volume threshold.

14. The computer system of claim 11, wherein the one or more processors are further configured to:
assign a traffic score to the current traffic data associated with each route segment the one or more route segments of each route of the plurality of routes between the origin location and the destination location to represent a level of congestion along the one or more segment; and
identify the one or more indications of calmness associated with each route segment of the one or more route segments based at least in part on the traffic score associated with each route segment of the one or more route segments.

15. A non-transitory computer-readable medium storing executable instructions for generating a route that, when executed by at least one processor of a computer system, cause the computer system to perform operations comprising:
receiving a navigation request from an origin location to a destination location, wherein the navigation request includes an indication of a user preference of a user for a calm route;
identifying, based at least in part upon map data, a plurality of routes between the origin location and the destination location;
receiving sensor data associated with one or more route segments of each route of the plurality of routes between the origin location and the destination location;
identifying one or more indications of calmness associated with each route segment of the one or more route segments by analyzing the sensor data;
determining a calmness score associated with each route segment of the one or more route segments based upon the one or more identified indications of calmness associated with each route segment of the one or more route segments; and
selecting one of the plurality of routes between the origin location and the destination location based at least in part upon the calmness score associated with each route segment of the one or more route segments.

16. The non-transitory computer-readable medium of claim 15, wherein the calmness score is determined based at least in part upon a number of the one or more indications of calmness and a degree of calmness associated with each route segment of the one or more route segments.

17. The non-transitory computer-readable medium of claim 15, wherein the sensor data includes historical sensor data.

18. The non-transitory computer-readable medium of claim 15, wherein the sensor data includes current traffic data.

19. The non-transitory computer-readable medium of claim 18, wherein the sensor data was collected by one or more sensors,
wherein the sensor data includes at least one selected from a group consisting of: 1) heart rate data associated with operators of vehicles captured while driving a route segment, 2) noise data received from exteriors of vehicles traveling along a route segment, 3) accelerometer data indicative of hard braking and acceleration events captured along a route segment, and 4) traffic data along a route segment.

20. The non-transitory computer-readable medium of claim 18, wherein the operations further comprise:
assigning a traffic score to the current traffic data associated with each route segment the one or more route segments of each route of the plurality of routes between the origin location and the destination location to represent a level of congestion along the one or more segment; and
identifying the one or more indications of calmness associated with each route segment of the one or more route segments based at least in part on the traffic score associated with each route segment of the one or more route segments.

21. A system for generating a route, the system comprising:
a means for storing instructions; and
a means for performing operations comprising:
receiving a navigation request from an origin location to a destination location, wherein the navigation request includes an indication of a user preference of a user for a calm route;
identifying, based at least in part upon map data, a plurality of routes between the origin location and the destination location;
receiving sensor data associated with one or more route segments of each route of the plurality of routes between the origin location and the destination location;
identifying one or more indications of calmness associated with each route segment of the one or more route segments by analyzing the sensor data;
determining a calmness score associated with each route segment of the one or more route segments based upon the one or more identified indications of calmness associated with each route segment of the one or more route segments; and
selecting one route of the plurality of routes between the origin location and the destination location based at least in part upon the calmness score associated with each route segment of the one or more route segments.

\* \* \* \* \*